United States Patent [19]

Kitakado et al.

[11] Patent Number: 5,408,538
[45] Date of Patent: Apr. 18, 1995

[54] METHOD OF AND APPARATUS FOR INSPECTING THE MINIMUM ANNULAR WIDTH OF A LAND ON A PRINTED CIRCUIT BOARD

[75] Inventors: Ryuji Kitakado; Hisayuki Tsujinaka; Tetsuo Hoki; Takao Omae, all of Kyoto, Japan

[73] Assignee: Dainippon Screen Mfg. Co., Ltd., Kyoto, Japan

[21] Appl. No.: 283,982

[22] Filed: Aug. 1, 1994

Related U.S. Application Data

[63] Continuation of Ser. No. 790,425, Nov. 12, 1991, abandoned.

[30] Foreign Application Priority Data

Nov. 27, 1990 [JP] Japan .................. 2-327161
Jul. 12, 1991 [JP] Japan .................. 3-198471

[51] Int. Cl.⁶ .................. G01G 11/02; G06K 9/36
[52] U.S. Cl. .................. 382/8; 382/25; 348/87; 348/126; 356/237
[58] Field of Search .................. 382/8, 25, 27, 16; 356/379, 380, 237; 364/564; 348/86, 87, 125, 127, 133

[56] References Cited

U.S. PATENT DOCUMENTS 4,040,748 8/1977 Belleson et al. .................. 356/199
4,223,387 9/1980 Danielsson et al. .................. 382/8
4,481,664 11/1984 Linger et al. .................. 382/8
4,555,798 11/1985 Broadbent, Jr. et al. .................. 382/8
4,980,570 12/1990 Yasunaga et al. .................. 250/561
5,027,417 6/1991 Kitakado et al. .................. 382/8
5,119,434 6/1992 Bishop et al. .................. 382/8

FOREIGN PATENT DOCUMENTS 2321229 8/1975 France .
3925911 7/1991 Germany .
2047879 12/1980 United Kingdom .

Primary Examiner—Leo H. Boudreau
Assistant Examiner—Larry J. Prikockis
Attorney, Agent, or Firm—Ostrolenk, Faber, Gerb & Soffen

[57] ABSTRACT

A printed pattern is provided with a wiring pattern having a land and a through hole surrounded by the land. The wiring pattern and the through hole are read by a photoelectric image sensor to obtain a pattern image and a hole image, respectively. A pattern gauge image is defined by the pattern image, and a hole gauge image having a ring-like shape is obtained from the hole image. A logical product between the inversion image of the pattern gauge image and the hole gauge signal provides a protrusion region image. An operator is applied to the protrusion region image in order to measure the minimum annular width by determining if the operator fits completely within the protrusion region. Since the hole gauge image has an isotropic contour, the minimum annular width of the land is detected, independent of the direction in which the through hole is deviated from the land.

22 Claims, 22 Drawing Sheets $Lb = Lt - La < 0$

METHOD OF AND APPARATUS FOR INSPECTING THE MINIMUM ANNULAR WIDTH OF A LAND ON A PRINTED CIRCUIT BOARD

This is a Continuation of application Ser. No. 07/790,425 filed on Nov. 12, 1991, now abandoned.

BACKGROUND OF THE INVENTION

1. Field of the Invention

The present invention relates to a method of and an apparatus for inspecting the minimum annular width of a land formed on a printed circuit board, and more particularly to an improvement to reconcile accuracy and speed in the inspection.

2. Description of the Prior Art

A printed circuit board is formed with wiring patterns having lands and through holes. Automatic inspection apparatus for the printed circuit board have been developed to automatically inspect the relative formation positions of the wiring patterns and through holes by reading the image of the printed circuit board and have been put to practical use. One of the significant inspection items in the printed circuit board inspection is the minimum annular width of a land which remains after forming a through hole therein.

FIG. 28 illustrates an example of the conventional inspection of an annular width of a land. There is formed a through hole 2 in a land 1. The through hole 2 is deviated from the center of the land 1 resulting from a drilling error and the like. During the inspection of the annular width, the binary images of a wiring pattern including the land 1 and the through hole 2 are obtained. A radial operator 3 is positioned such that its center coincides with the center of the through hole 2. A logical operation is performed between the radial operator 3 and the image of the wiring pattern. The radial operator 3 has a plurality of arms. The annular widths of the wiring pattern in the elongated directions of the respective arms are determined from the logical operation results on the arms. Then, a minimum annular width $W_L$ which is the minimum value among the respective annular widths is obtained. When the minimum annular width $W_L$ is smaller than a threshold value, it is determined that the printed circuit board is defective. Such a radial operator is disclosed in Japanese Patent Application Laid-Open No. 62-263404, for example.

The direction in which the through hole 2 is deviated from the land 1 is not constant and varies in respective printed boards to be inspected. In order to accurately determine the is minimum annular width, it is necessary to increase the number of arms of the radial operator 3. The increase in the number of arms causes the time period required for the logical operation to grow increase so that the inspection is prevented from being performed at a high speed. Another problem is that the costs for manufacturing the inspection apparatus rise.

SUMMARY OF THE INVENTION

The present invention is directed to a method of inspecting the minimum annular width of a land formed on a printed circuit board. The printed board is provided thereon with a wiring pattern having the land and a through hole perfectly or imperfectly surrounded by the land.

According to the present invention, the method comprises the steps of: (a) obtaining a pattern image representing the shape of the wiring pattern and a hole image representing the shape of the through hole; (b) converting the hole image into a hole gauge image having an isotropic contour; (c) obtaining a pattern gauge image having a contour of the same shape as the pattern image; (d) obtaining a protrusion region image representative of part of the hole gauge image which protrudes from the pattern gauge image; and (e) comparing the size of the protrusion region image with a predetermined reference value to determine whether the minimum annular width of the land is larger than the reference value or not.

In an aspect of the present invention, the pattern gauge image is obtained through the step of: (c-1) defining the pattern gauge image by the pattern image itself.

The hole gauge image may be generated through the steps of: (b-1) enlarging the hole image by first and second enlargement widths different from each other to obtain first and second enlarged hole images, respectively; and (b-2) logically combining the first and second enlarged hole images to form a ring-like image around the hole image, the ring-like image being defined as the hole gauge image.

In another aspect of-the present invention, the hole gauge image is obtained through the step of: (b-3) enlarging the hole image to define the hole gauge image.

The pattern gauge image may be obtained through the steps of: (c-2) logically combining the pattern image and the hole image to obtain a corrected image; and (c-3) obtaining the pattern gauge image from the corrected image.

The present invention also provides an apparatus adapted to conduct the present method.

The deviation of the center of the though hole from the center of the land has a complementary relationship with the minimum annular width, which is defined as the minimum value among annular widths at respective positions on the land. That is, the former is small when the latter is large, and vice versa. When the minimum annular width is large, the deviation of the center of the through hole from the center of the land is small, so that the hole gauge image having the isotropic contour does not protrude or protrudes slightly from the pattern gauge image having the contour of the same shape as the pattern image. Accordingly, the size of the protrusion region image is zero or small.

When the minimum annular width is small, the size of the protrusion region image is large. In the present invention, the size of the protrusion region image is compared with the reference value to decide whether the minimum annular width is sufficient or not.

The process step of comparing the size of the protrusion region image with the reference value may be attained by applying an operator having a size corresponding to the reference value to the protrusion region image.

According to the present invention, since the minimum annular width is inspected by inspecting the size of the protrusion region image without applying a radial operator having arms to the land itself, the minimum annular width can be inspected accurately regardless of the direction in which the through hole is deviated from the land. Thus, a high-speed inspection can be achieved.

An automatic inspection device for the printed circuit board, when applied to the present invention, does not need a complicated circuit which causes costs to rise.

When an operator having a size corresponding to the reference value is applied to the protrusion region image, as in a preferred embodiment of the present invention, the minimum annular width is inspected simply and accurately.

Employment of the ring-like image obtained from the first and second enlarged hole images prevents the false decision resulting from the influence of a gap which may appear between the pattern image and the hole image.

The reference value may be variable. In this case, the sizes of the operator and ring-like image are accordingly changed. This prevents false detection resulting from the broken pattern image when the minimum annular width is extremely small.

On the other hand, when the hole gauge image is defined by enlarging the hole image, the substantial decrease of the minimum annular width due to employment of the first enlarged hole image can be eliminated to achieve a more accurate inspection.

Further, when the pattern gauge image is defined by a corrected image obtained by combining the pattern image and the hole image, a false detection around the hole is prevented.

The corrected image may be thickened and then shrinked to obtain the pattern gauge image, so that a gap which may appear in the corrected gauge image is eliminated to achieve a more accurate inspection.

Accordingly, an object of the present invention is to provide a method of and an apparatus for inspecting the minimum annular width of a land on a printed circuit board accurately at a high speed.

Another object of the present invention is to provide an apparatus for inspecting a printed-board which can be obtained at a low cost.

These and other objects, features, aspects and advantages of the present invention will become more apparent from the following detailed description of the present invention when taken in conjunction with the accompanying drawings.

DESCRIPTION OF THE PREFERRED EMBODIMENTS

A. Image Reading

Figure 4:
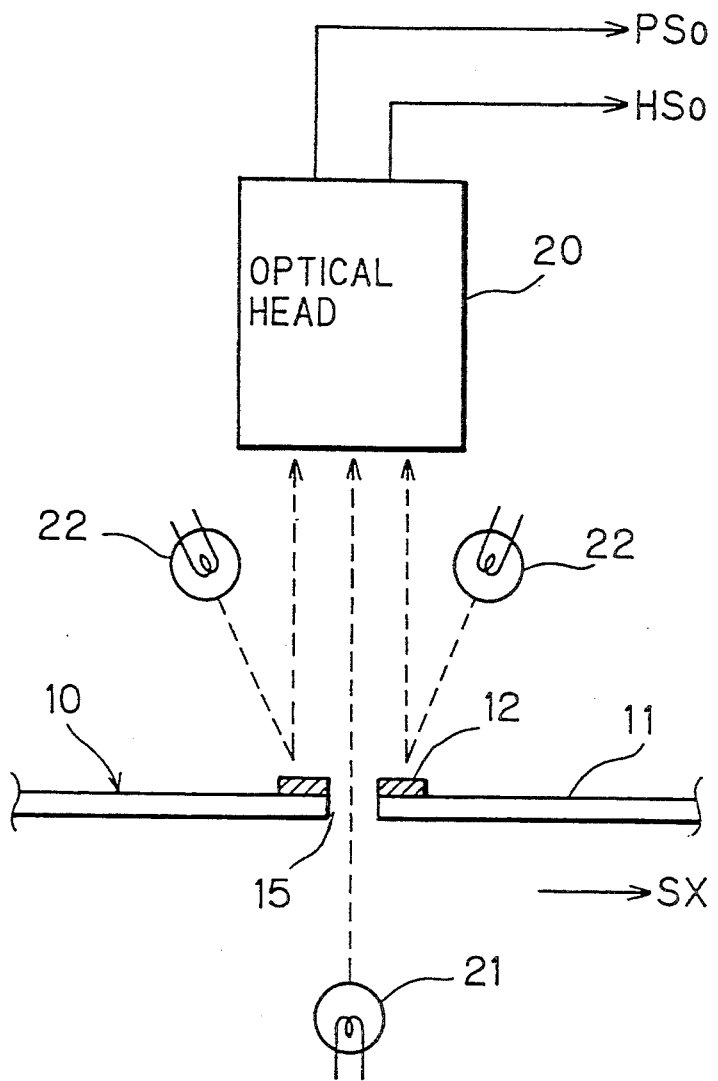
FIG. 4 shows an optical system for obtaining the image of a printed circuit board.

FIG. 4 schematically shows an image reading unit of an automatic inspection device for a printed circuit board according to a preferred embodiment of the present invention. A printed circuit board 10 is formed with a conductive wiring pattern 12 on one or both surfaces of an insulative base plate 11. As shown in the plan view of FIG. 5, the wiring pattern 12 includes a line part 13 and a land 14. There is provided a through hole 15 piercing the land 14 and insulative base plate 11.

Figure 5:
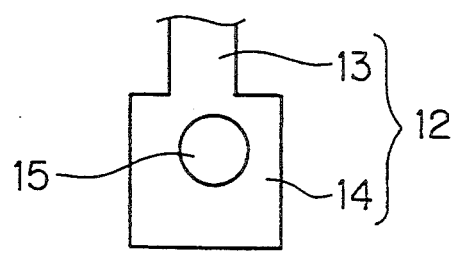
FIG. 5 illustrates relationship between a land and a through hole.

The through hole 15 shown in FIGS. 4 and 5 is a normal through hole for mounting electronic parts therethrough, which has a relatively large diameter. A through hole of another type is a mini via hole for connection between both surfaces of the printed circuit board 10, which has a relatively small diameter. Both the normal through hole and the mini via hole are generically referred to as "through holes" in the present invention.

A transmission light source 21 is disposed below the printed circuit board 10, while reflection light sources 22 are disposed above the printed circuit board 10. Light from the transmission light source 21 passes through the through hole 15 to reach an optical head 20. Light from the reflection light sources 22 is reflected from the surface of the printed circuit board 10 to reach the optical head 20. The transmission and reflection light sources 21 and 22 are adapted to emit lights having different wavelengths. The lights pass through an image-formation lens system provided in the optical head 20 and are separated from each other by a dichroic mirror. Two CCD arrays also provided in the optical head 20 detect the separated lights, respectively. Each of the CCD arrays transforms the light into an electric signal to produce a pattern image signal $PS_0$ representative of the wiring pattern 12 and a hole image signal $HS_0$ representative of the through hole 15. Scanning for reading the images of respective parts of the printed circuit board 10 can be achieved by moving the printed circuit board 10 in the horizontal direction SX of FIG. 4.

B. Outline of Inspection Circuit

Figure 6:
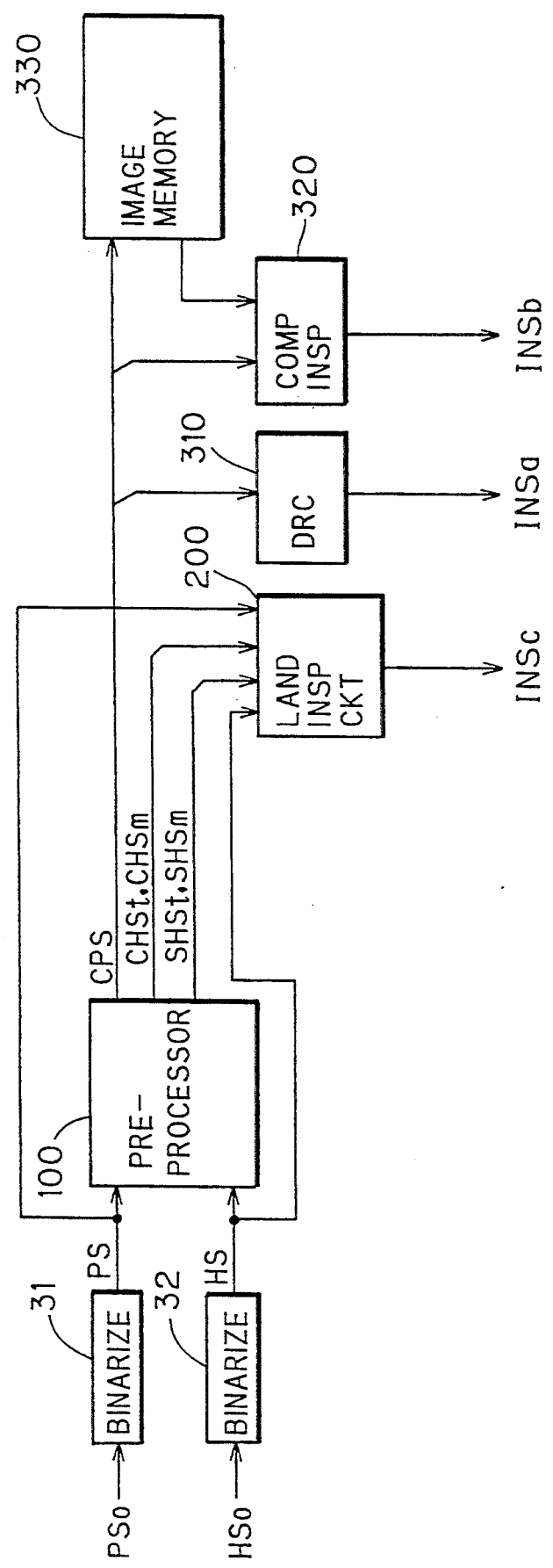
FIG. 6 is a block diagram of an electric circuitry employed in the apparatus, according to the respective preferred embodiments.

The pattern image signal $PS_0$ and the hole image signal $HS_0$ are delivered to binarizing circuits 31 and 32 of FIG. 6, respectively. The binarizing circuit 31 binarizes the pattern image signal $PS_0$ by comparing the pattern image signal $PS_0$ with a first threshold value TH1 shown in FIG. 7(a) to produce a digital pattern image signal PS. The binarizing circuit 32 compares the hole image signal $HS_0$ with a second threshold value TH2 to convert the hole image signal $HS_0$ into a digital hole image signal HS binarized.

Figure 7:
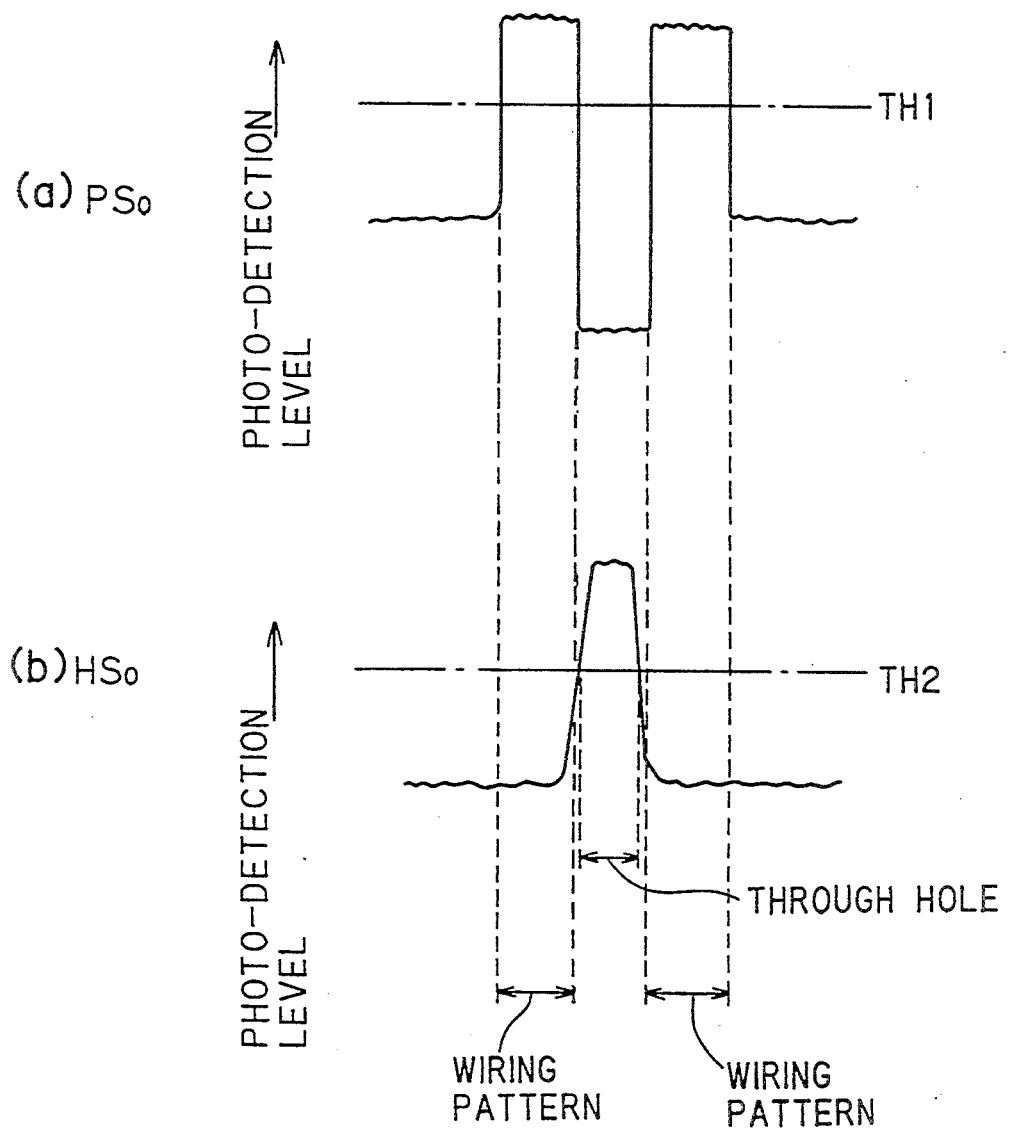
FIG. 7 is a waveform chart showing the binarization of a pattern image and a through hole.
Figure 8:
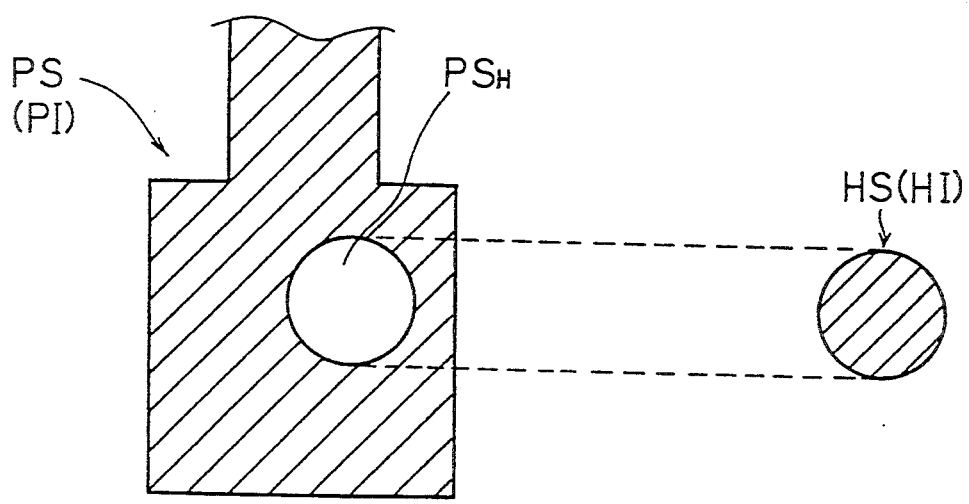
FIGS. 8 and 9 show size relationship between a blank portion of the pattern image and the through hole, respectively.
Figure 9:
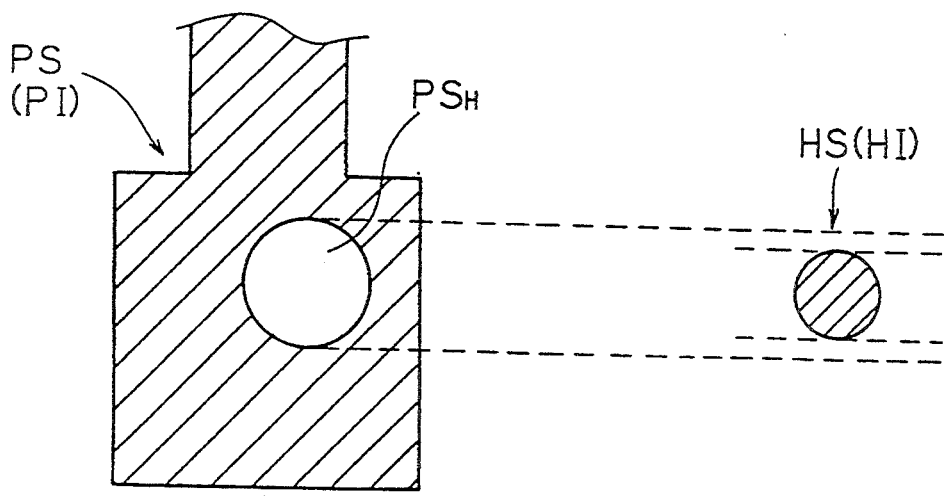

It is ideal that the size of a blank portion $PS_H$ (FIG. 8) of the pattern image represented by the pattern image signal PS should be equal to that of a hole image HI represented by the hole image signal HS. However, the edge portions of the analog hole image signal $HS_0$ are inclined as shown in FIG. 7(b) resulting from light reflection from the inner wall of the through hole 15 and the like. As a result, the size of the obtained hole image HS is not equal to and is smaller than that of the blank portion $PS_H$ as shown in FIG. 9. An improvement for compensating the deviation through data processing will be described later.

With reference again to FIG. 6, the binarized pattern image signal PS and hole image signal HS are delivered to a pre-processor 100. The pre-processor 100 produces signals $CHS_t$, $CHS_m$, $SHS_t$ and $SHS_m$, which will be described later, to output them to a land inspection circuit 200. The pattern image signal PS and the hole image signal HS are also inputted to the land inspection circuit 200. The details of the land inspection circuit 200 will be also described later. The inspection result of the land inspection circuit 200 is outputted as an inspection result signal $INS_c$.

The pre-processor 100 supplements and reshapes the blank portion of the pattern image by performing a compensation processing on the pattern image signal PS to thereby produce a corrected pattern image signal CPS. The corrected pattern image signal CPS is supplied to a DRC (Design Rule Check) circuit 310 and to a comparative inspection circuit 320. The DRC circuit 310 extracts the characteristics of the pattern image and compares them with the CAD data of the printed circuit board. The comparative inspection circuit 320 compares the pattern image of the printed circuit board to be inspected with a non-defective pattern image previously stored in an image memory 330 to execute an appearance inspection of the printed circuit board. The inspection results of the circuits 310 and 320 are outputted as inspection result signals $INS_a$ and $INS_b$, respectively.

C. Details of Pre-processor 100

Figure 10:
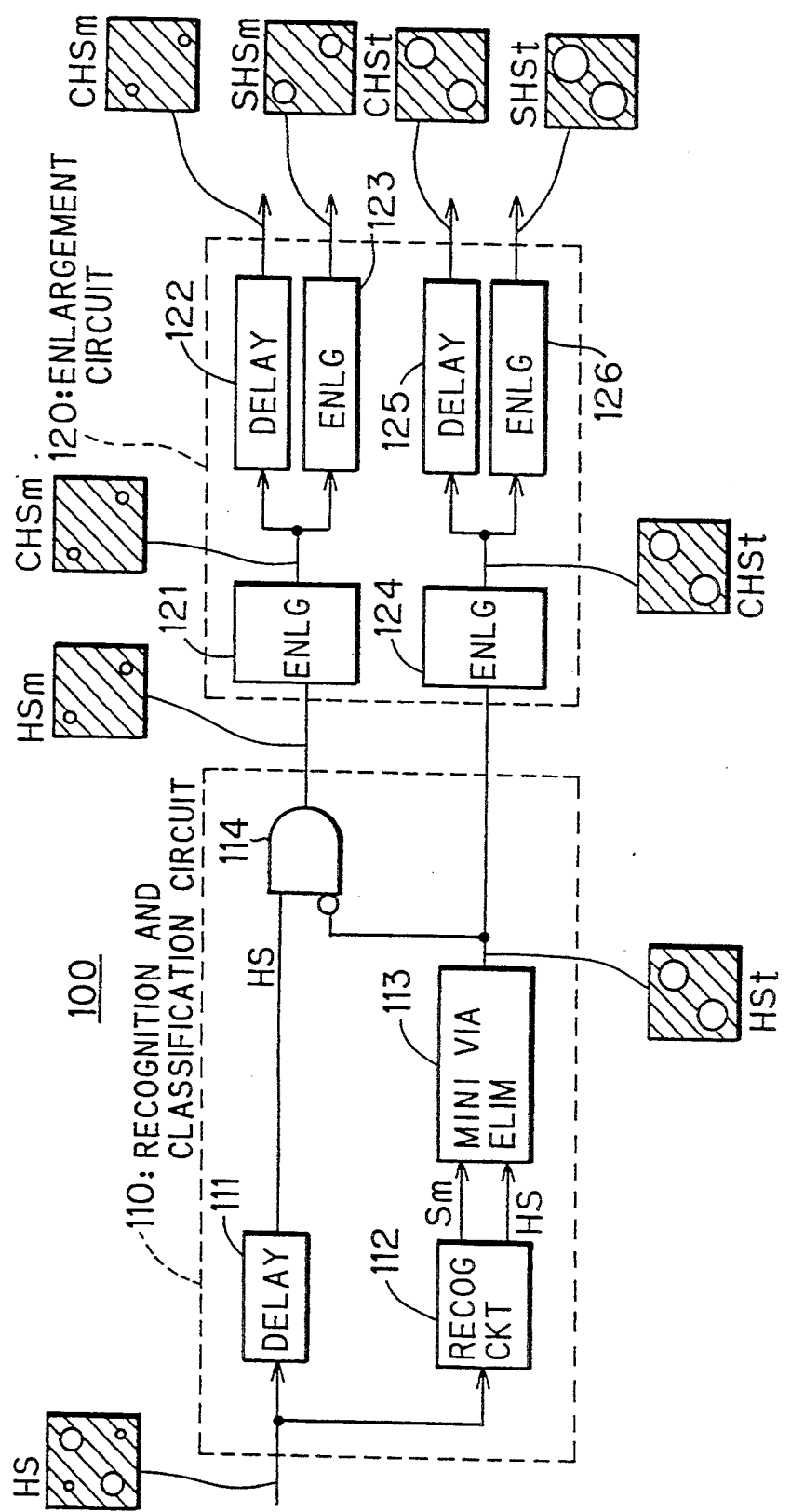
FIG. 10 is a block diagram of a pre-processor.

There is shown in detail in FIG. 10 part of the preprocessor 100 relevant to the processing of the hole image signal HS. The hole image signal HS is given to a recognition circuit 112 in a recognition and classification circuit 110. The recognition circuit 112 detects the diameter of the through hole 15 by applying a cross-shaped operator to the hole image and recognizes whether the through hole 15 is a normal through hole or a mini via hole by comparing the diameter with a predetermined threshold value. The recognition result is indicated by a signal $S_m$.

The signal $S_m$ and the hole image signal HS are outputted to a mini via hole elimination circuit 113. The mini via hole elimination circuit 113 fills in the inside of the mini via hole to thereby produce a hole image signal $HS_t$ including only the normal through hole.

The hole image signal HS is also sent to a delay circuit 111 and is delayed therein, so that timing is adjusted between the hole image signal HS and the signal $HS_t$. The logical product of an inversion signal of the signal $HS_t$ and the signal HS is obtained in an AND circuit 114. Logical product signal $HS_m$ is a hole image signal including only the mini via hole. It should be noted that, for ease of illustration, the cross-hatching in FIG. 10 represents regions having a logic value "0" while the blank areas in FIG. 10 represent regions having a logic value "1". The contrary rule applies to FIGS. 8 and 9, in which the cross-hatched areas represent regions having a logical value "1".

The hole image signals $HS_t$ and $HS_m$ are inputted to an enlargement circuit 120. The hole image signal $HS_m$ representative of the mini via hole is enlarged by the width of a predetermined number of pixels, e.g., by the width of one pixel, in an enlargement circuit 121 to be converted into the first enlarged hole image signal $CHS_m$ for the mini via hole. The first enlarged hole image signal $CHS_m$ is further enlarged in an enlargement circuit 123 to be converted into the second enlarged hole image signal $SHS_m$. The first enlarged hole image signal $CHS_m$ which is subjected to a timing adjustment in a delay circuit 122 and the second enlarged hole image signal $SHS_m$ are outputted to the exterior of the enlargement circuit 120.

Similarly, the hole image signal $HS_t$ representative of the normal through hole is enlarged by the width of a predetermined number of pixels, e.g., by the width of one pixel, in an enlargement circuit 124 to be converted into the first enlarged hole image signal $CHS_t$ for the normal through hole. The first enlarged hole image signal $CHS_t$ is further enlarged in an enlargement circuit 126 to be converted into the second enlarged hole image signal $SHS_t$. The first enlarged hole image signal $CHS_t$ which is subjected to a timing adjustment in a delay circuit 125 and the second enlarged hole image signal $SHS_t$ are outputted from the enlargement circuit 120.

Figure 11:
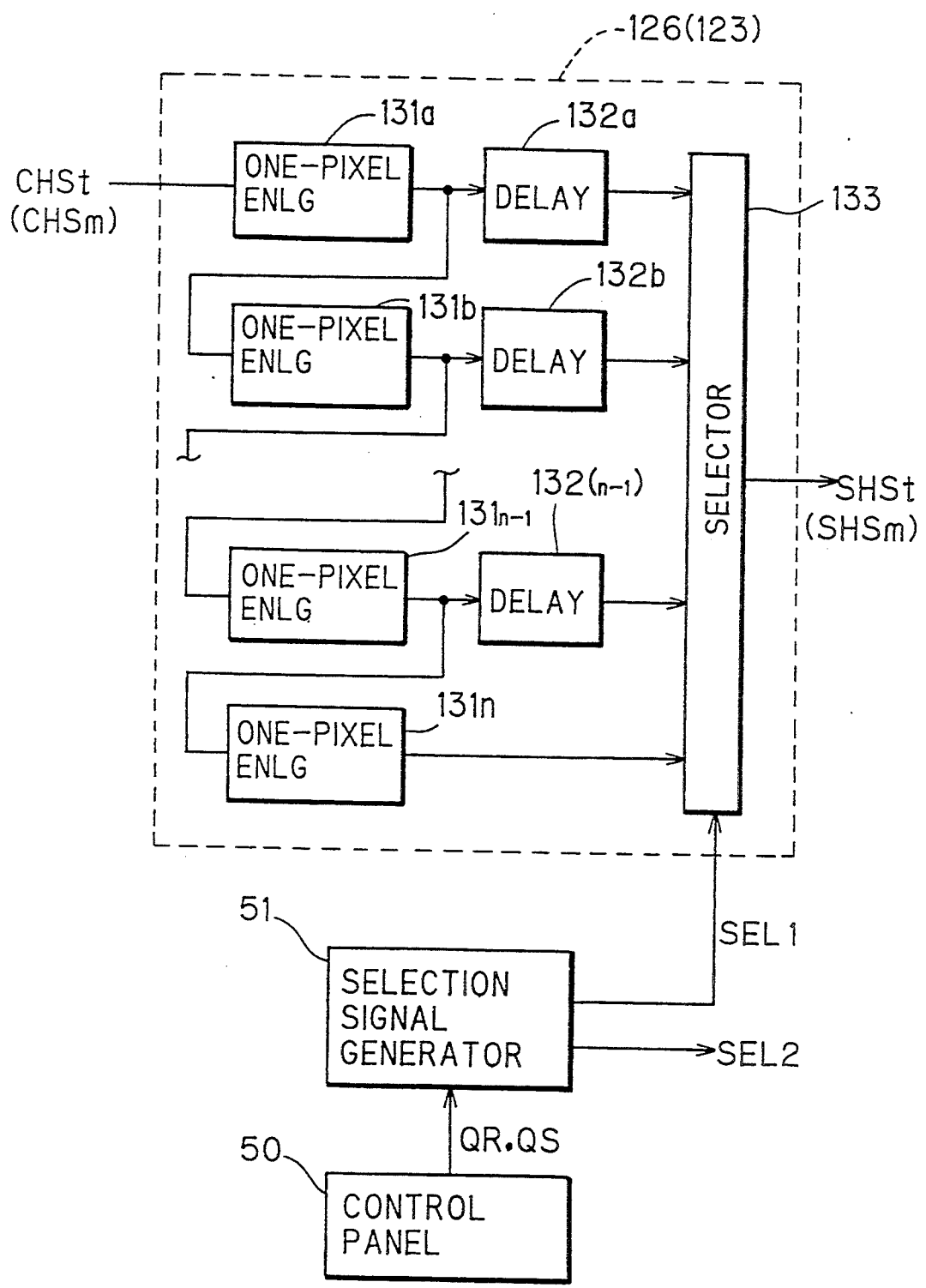
FIG. 11 is a block diagram of a variable enlargement circuit.

FIG. 11 is a block diagram of the internal structure of the enlargement circuit 126 for executing the second enlargement on the hole image of the normal through hole. The enlargement circuit 123 for the mini via hole has the same structure. The enlargement circuit 126 includes one-pixel enlargement circuits 131a to 131n for further enlarging the first enlarged hole image by the width of one pixel in sequential order. The number of one-pixel enlargement circuits 131a to 131n is, for example, twenty. All but the last one-pixel enlargement circuit 131n are fitted with delay circuits 132a to 132(n-1) for timing adjustment. The one-pixel enlargement circuits 131a to 131n are connected in series, and the respective outputs thereof are given to a selector 133 in parallel. Thus the selector 133 receives n-number of enlarged hole image signals which are obtained by enlarging the first enlarged hole image signal $CHS_t$ by the width of i-number of pixels (i=1 to n). Each of the one-pixel enlargement circuits 131a to 131n is adapted to perform a one-pixel enlargement processing in accordance with eight-point neighborhood enlargement logic, for example.

The printed circuit board inspection apparatus according to the preferred embodiment is equipped with a control panel 50. Through manual operation of the control panel 50, a reference value designation signal QR and an operator size designation signal QS described later are inputted to a selection signal generator 51. The selection signal generator 51 produces a selection signal SEL1 based on the operator size designation signal QS to send it to the selector 133. The selector 133 outputs one of the n-number of enlarged hole image signals in response to the selection signal SEL1 as the second enlarged hole image signal $SHS_t$.

Hence, the enlargement circuits 126 and 123 are variable enlargement circuits capable of changing the enlargement width.

D. Details of Land Inspection Circuit 200

Figure 12:
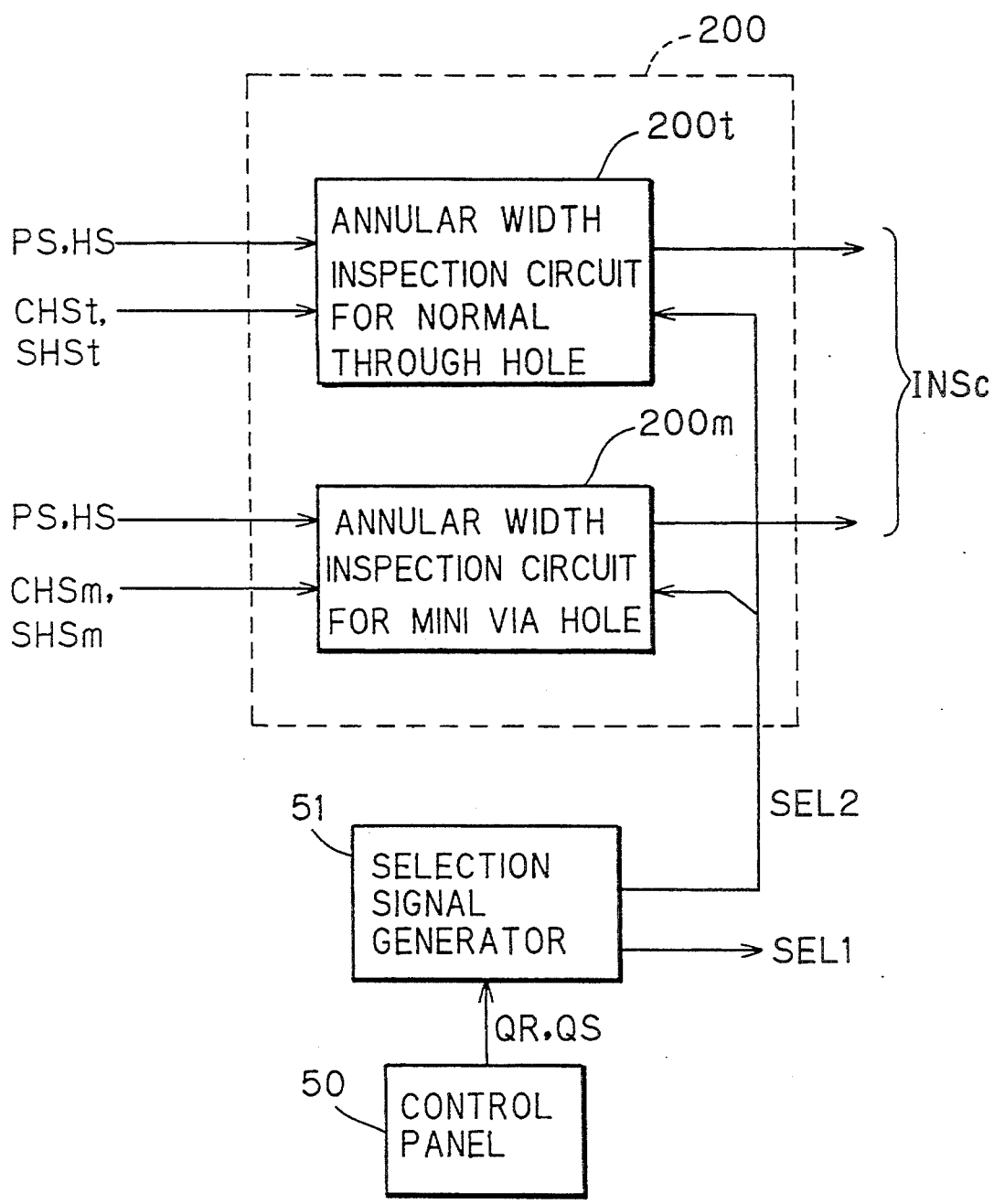
FIG. 12 is a block diagram of a land inspection circuit.

FIG. 12 is a block diagram of part of the land inspection circuit 200 relevant to the preferred embodiment of the present invention. The land inspection circuit 200 includes an annular width inspection circuit 200t for the normal through hole and an annular width inspection circuit 200m for the mini via hole. The annular width inspection circuits 200t and 200m have the same internal structure and hold different data values such as reference values for inspecting the annular widths of through holes. Although only the annular width inspection circuit 200t is described hereinafter, the structure and the operation of the other circuit 200m will be understood by those skilled in the art from the following description.

Figure 1:
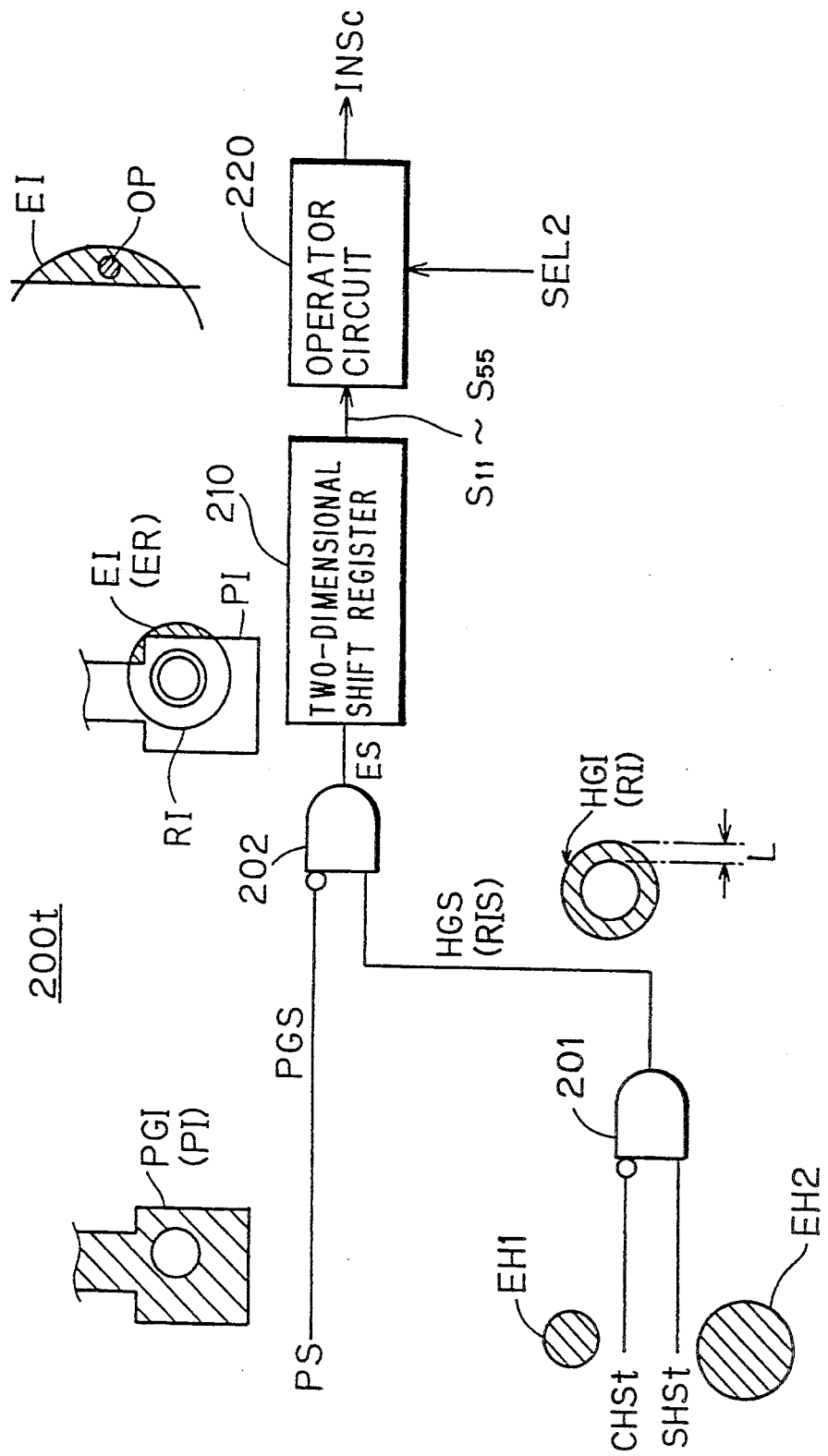
FIGS. 1 to 3 are block diagrams of structures for obtaining an image of a protrusion region and applying an operator to the image of the protrusion region according to first to third preferred embodiments of the present invention, respectively.

There is shown in FIG. 1 an example of the internal structure of the annular width inspection circuit 200t. A pattern gauge signal PGS is obtained from the pattern image signal PS. Although the pattern gauge signal PGS is identical to the pattern signal PS in the preferred embodiment, the pattern gauge signal PGS may be a signal not identical but similar to the pattern signal PS. The pattern gauge signal PGS represents a pattern gauge image PGI, which is identical to the pattern image PI, in the preferred embodiment. The pattern gauge image signal PGS is inverted and input into an AND circuit 202. Another input of the AND circuit 202 is a hole gauge signal HGS representing a hole gauge image HGI. In this example, the hole gauge image HGI is a ring-like image RI, which is obtained by taking a logical product of an inversion signal of the first enlarged hole image signal $CHS_t$ and the second enlarged hole image signal $SHS_t$. The output signal HGS (RIS) of the AND circuit 201 represents the ring-like image RI obtained by removing the first enlarged hole image EH1 from the second enlarged hole image EH2. The pattern gauge image PGI and the hole gauge image HGI reflect the shapes of the pattern image PI and the hole image HI, respectively.

When the inversion signal of the pattern gauge signal PGS and the hole gauge signal HGS are applied to the AND circuit 202, the AND circuit 202 outputs a signal ES. The signal ES is a "protrusion region image signal" representative of part of the hole gauge image HGI which does not overlap the pattern gauge image PGI, that is, representative of a region ER protruding from the pattern gauge image PGI in the hole gauge image HGI. The protrusion region image signal ES is input to a two-dimensional shift register 210 for each pixel in series.

Figure 13:
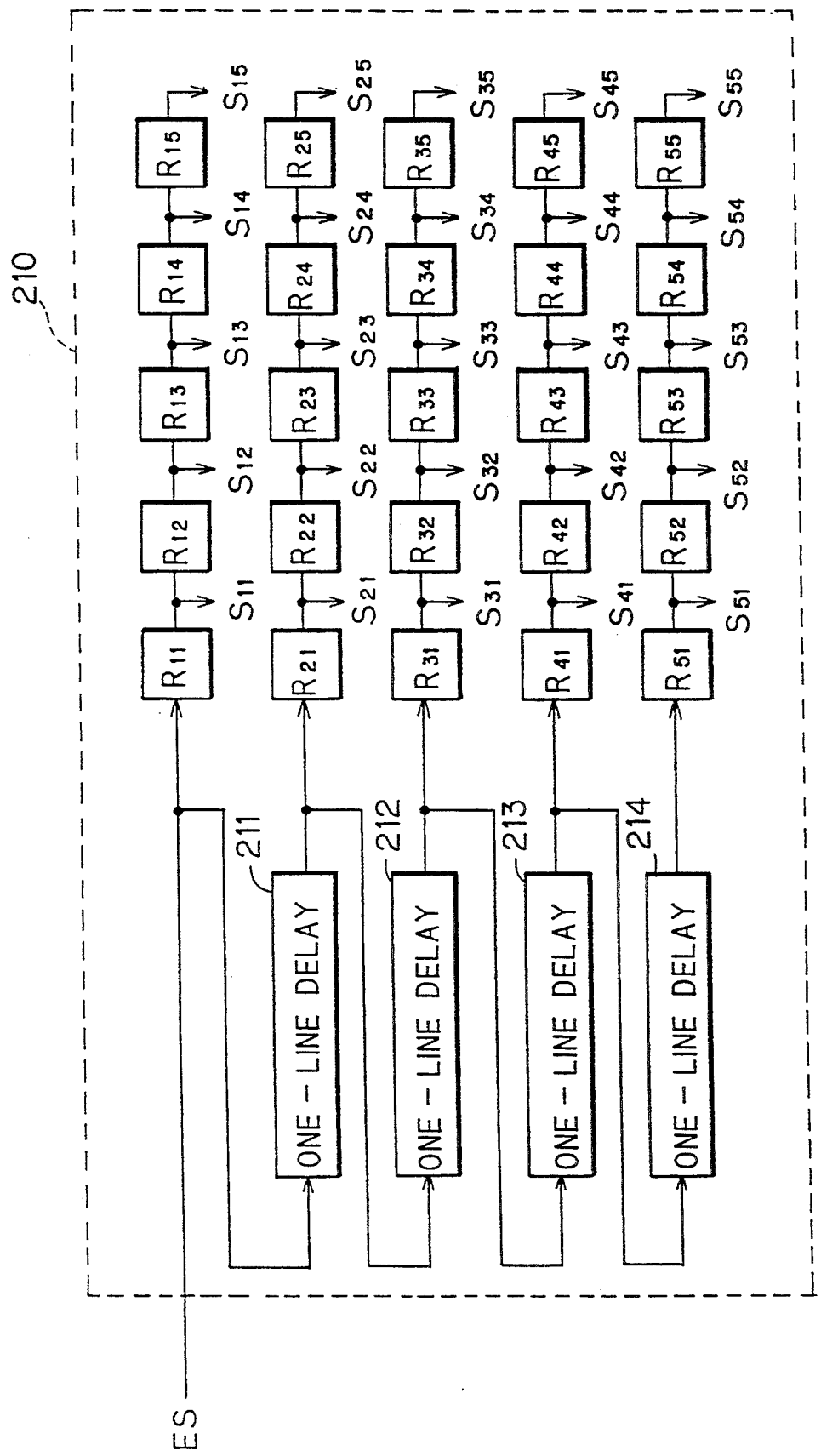
FIG. 13 is a block diagram of a two-dimensional shift register.

As shown in FIG. 13, the two-dimensional shift register 210 includes four one-line delay circuits 211 to 214 and twenty-five unit registers $R_{11}$ to $R_{55}$ arranged in a 5×5 matrix form. Outputs $S_{11}$ to $S_{55}$ from the unit registers $R_{11}$ to $R_{55}$ correspond to the two-dimensional protrusion region image signal ES in a 5×5 pixel arrangement. The signals $S_{11}$ to $S_{55}$ are transmitted to an operator circuit 220 (FIG. 1) in parallel.

Figure 14:
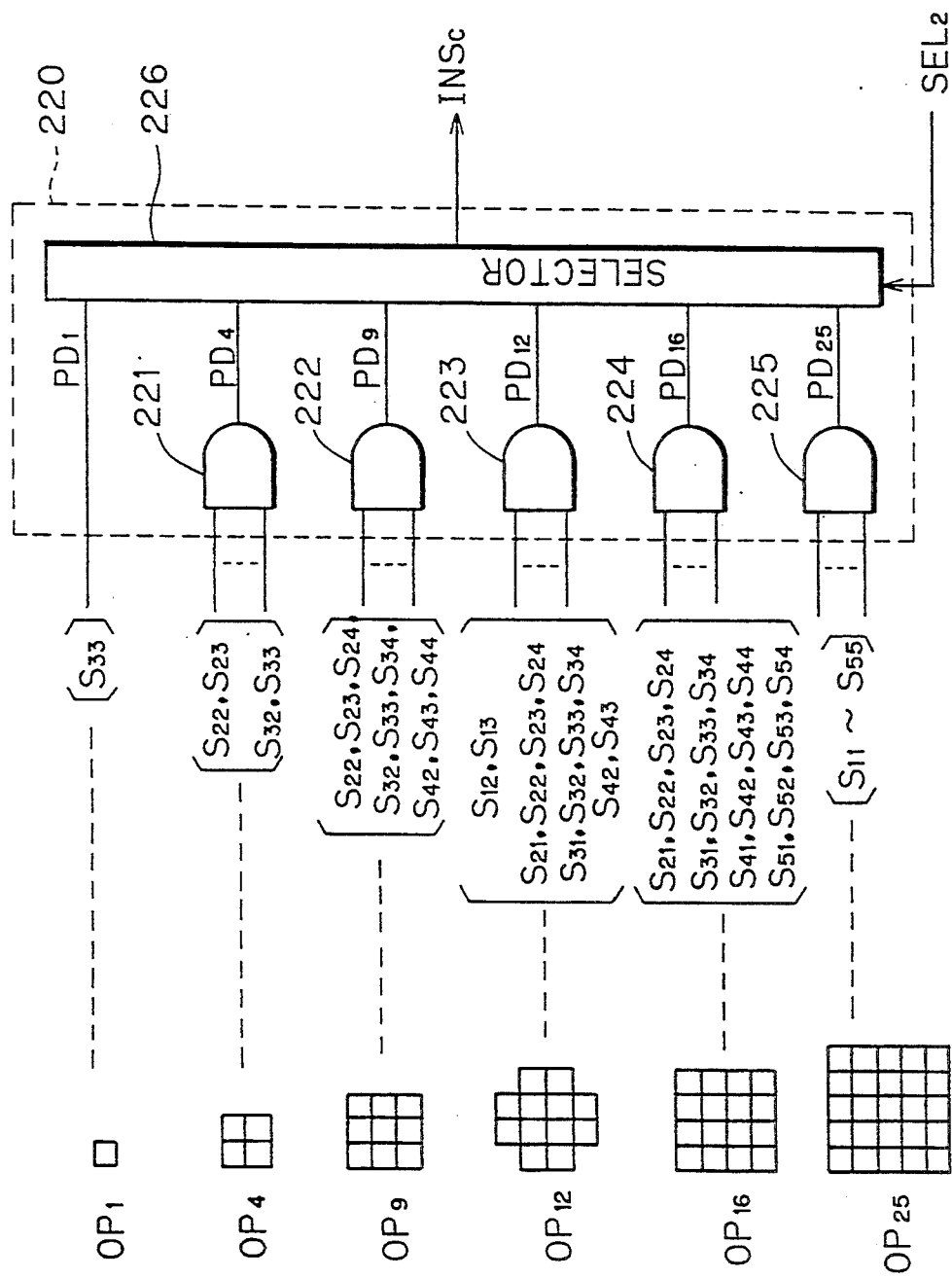
FIG. 14 is a block diagram of an operator circuit.

The operator circuit 220 includes AND circuits 221 to 225 and a selector 226, as shown in FIG. 14. The AND circuit 221 receives the signals $S_{22}$, $S_{23}$, $S_{32}$ and $S_{33}$ constituting a 2×2 pixel matrix $OP_4$ and outputs the logical product $PD_4$ of the signals to the selector 226. Only when the pixel matrix $OP_4$ is positioned on a protrusion region image EI of FIG. 1, the logical product $PD_4$ is "1". For this reason, the pixel matrix $OP_4$ is an operator for a 2×2 pixel arrangement.

The other AND circuits 222 to 225 operate similarly to the AND circuit 221. When an operator $OP_9$ for a rectangular cluster of nine pixels, an operator $OP_{12}$ for a cross-shaped cluster of twelve pixels, an operator $OP_{16}$ for a rectangular cluster of sixteen pixels, and an operator $OP_{25}$ for a rectangular cluster of twenty-five pixels are applied to the protrusion region image EI, their outputs are given to the selector 226 as logical product signals $PD_9$, $PD_{12}$, $PD_{16}$ and $PD_{25}$, respectively. The signal $S_{33}$ is also inputted to the selector 226 as a signal $PD_1$. The signal $PD_1$ corresponds to the operation result of an operator $OP_1$ having only one pixel.

The selection signal generator 51 of FIG. 12 produces a selection signal SEL2 in response to the reference value designation signal QR and operator size designation signal QS and outputs the selection signal SEL2 to the selector 226 of FIG. 14. The selector 226 selects one of the input signals $PD_1$ to $PD_{25}$ in response to the designation of the selection signal SEL2 to output the selected signal as the inspection result signal $INS_C$.

This electrical operation corresponds to an operation for determining the minimum annular width of the through hole. The reason therefor will be described later in detail. Hereinafter, the operators $OP_1$ to $OP_{25}$ are represented by the reference character "OP", and the logical product signals $PD_1$ to $PD_{25}$ are represented by the reference character "PD".

E. Principle of Determining Minimum Annular Width

Figure 15:
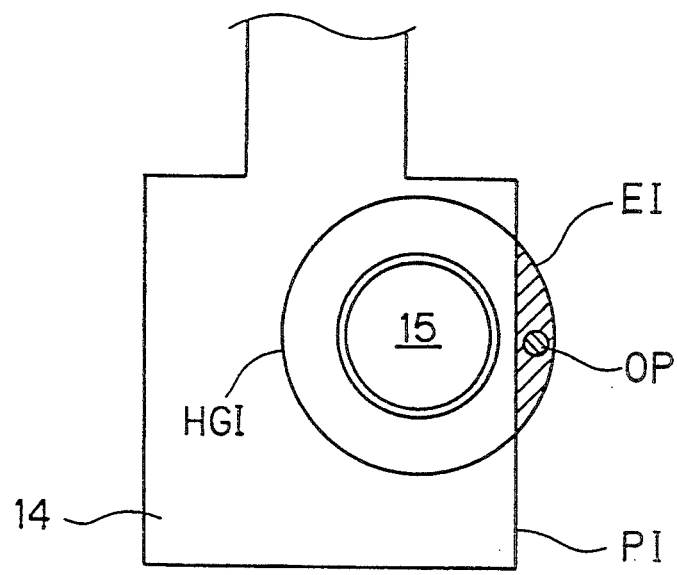
FIGS. 15 to 18 illustrate the principle of detecting a minimum annular width.

The operator OP corresponds to an approximately circular small region as shown in FIG. 15 since it is composed of a cluster of pixels. The logical product of "1" which is the result of applying the operator OP to the protrusion region image EI means that the size of the protrusion region image EI is larger than that of the operator OP. Since the center of the hole gauge image HGI coincides with the center of the through hole 15, the protrusion region image EI of large size is equivalent to the large deviation of the through hole 15 from the center of the land 14 so that the minimum annular width of the land 14 is small.

Figure 16:
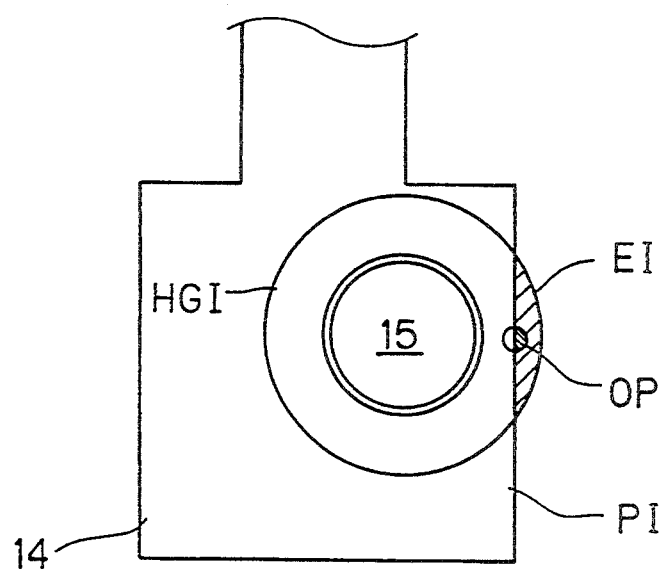

On the other hand, when the deviation of the through hole 15 from the center of the land 14 is small as shown in FIG. 16, the size of the protrusion region image EI is small. In this case, the whole operator OP is not present within the protrusion region image EI, so that the result of applying the operator OP to the protrusion region image EI is constantly "0". Hence, if the signal PD of "1" is detected while the operator OP is scanning the protrusion region image EI, it is concluded that the minimum annular width is insufficient and the printed board is defective. Conversely, if the signal PD is always "0" during the scan, it is concluded that the minimum annular width is sufficient and the printed board is not defective. The scanning by the operator OP on the protrusion region image EI is automatically achieved by the scanning for reading the image of the printed circuit board 10.

Preferably, the operator OP is a perfectly or approximately circular in shape. It is, however, difficult to provide a perfectly circular operator in the digital signal processing. In this preferred embodiment, the rectangular operators or the cross-shaped operators obtained by removing the pixels at the corners from the rectangular operators are employed as approximately circular operators.

The reason for preparing the plurality of operators $OP_1$ to $OP_{25}$ and selectively using one of them will be described later.

Figure 17:
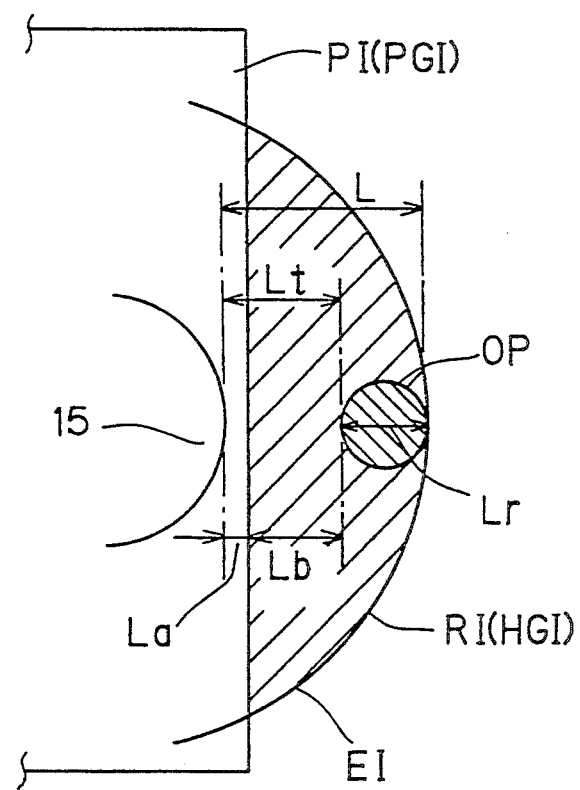

Next, the principle will be explained more quantitatively. Respective values shown in FIG. 17 are defined as follows:

$L_r$: size of the operator OP (diameter of the circle);

$L_t$: distance between the circumference of the through hole 15 and the operator OP;

$L$: width of the hole gauge image HGI;

$L_a$: minimum annular width of the land;

$L_b$: distance between the circumference of the operator OP and the edge of the pattern gauge image PGI.

The ring-like image RI described with reference to FIG. 1 may be used as the hole gauge image HGI. In this case, the width L is defined as the ring width of the ring-like image RI. Although the hole image HI and the blank portion $PS_H$ of the pattern image PI do not exactly coincide as discussed with reference to FIG. 9, it is assumed that they coincide approximately. The circumference of the blank portion $PS_H$ of the pattern image PI is taken as the circumference of the through hole 15. In another case, an enlarged hole image EHI is used as the hole gauge image HGI, as described below. In this case, it is unnecessary to take into consideration the blank portion $PS_H$ corresponding to the through hole 15 because the pattern gauge image PGI is a corrected pattern image CI in which the blank portion $PS_H$ is approximately compensated for (see FIGS. 2 and 3) or a corrected pattern image DI in which the blank portion $PS_H$ is completely compensated for (see FIG. 2). Thus, the width L may be considered as the result of subtracting the radius of the through hole 15 (the radius of the hole image) from the radius of the enlarged hole image EHI.

As is apparent from FIG. 17, the following formulas hold:

$$L = L_r + L_t \quad (1)$$

$$L_t = L_a = L_b \quad (2)$$

Accordingly, $$L_a = L - L_r - L_b \quad (3)$$

On the other hand, a condition for ensuring the necessary minimum annular width is:

$$L_a \geq L_0 \quad (4)$$

where $L_0$ is a reference value of the minimum annular width.

Substitution of the formula (3) into the formula (4) gives:

$$L - L_4 - L_b \geq L_0 \quad (5)$$

Since the boundary between sufficient and insufficient minimum annular widths should correspond to the state in which the operator OP is just fitted into the protrusion region image EI and the distance $L_b$ of zero, the following formula is obtained as a criterion for discriminating the sufficient and insufficient minimum annular widths:

$$L - L_r L_0 \quad (6)$$

Figure 18:
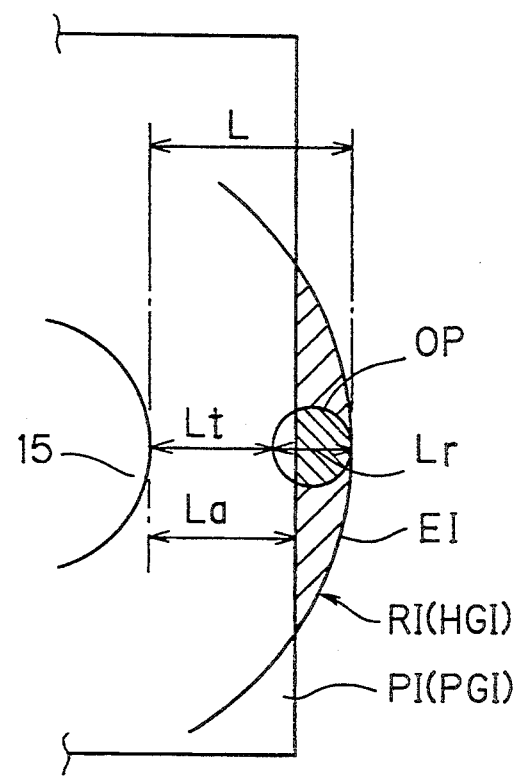

That is, the width L of the hole gauge image HGI and the size $L_r$ of the operator OP are determined so that the difference therebetween is equal to the reference value $L_0$ of the minimum annular width. This provides the result of "insufficient minimum annular width" because the formula (5) does not hold when the quantity $L_b$ is plus as shown in FIG. 17. On the other hand, the result of "sufficient annular width" is obtained because formula (5) holds when $L_b$ is substantially minus as shown in FIG. 18.

In this preferred embodiment, when the reference value $L_0$ is designated arbitrarily through the control panel 50 (FIG. 12), the signal QR representative of this value is input to the selection signal generator 51. The selection image HGI and the size $L_r$ of the operator OP according to signal generator 51 calculates the width L of the hole gauge the formula (6).

As is recognized from the formula (6), there are a plurality of pairs of values (L, $L_r$) satisfying the formula (6). In this preferred embodiment, six values are prepared for the size $L_r$ of the operator OP and one of them can be selected arbitrarily in response to the operator size designation signal QS. The preparation of the six operators $OP_1$ to $OP_{25}$ in the structure of FIG. 14 corresponds to the preparation of the six values for the size $L_r$. The operators $OP_1$ to $OP_{25}$ are different in size, and one of them is selected in response to the operator size designation signal QS. The reason for the variable size of the operator will be described later.

When the size $L_r$ of the operator is selected, the width L is uniquely determined from the formula (6). This determination can be achieved by storing a table generator 51. Preferably, different sets of values (L, $L_r$, corresponding to the formula (6) in the selection signal $L_0$) are used for the normal through hole and the mini via hole.

F. Production of Hole Gauge Image

Figure 26:
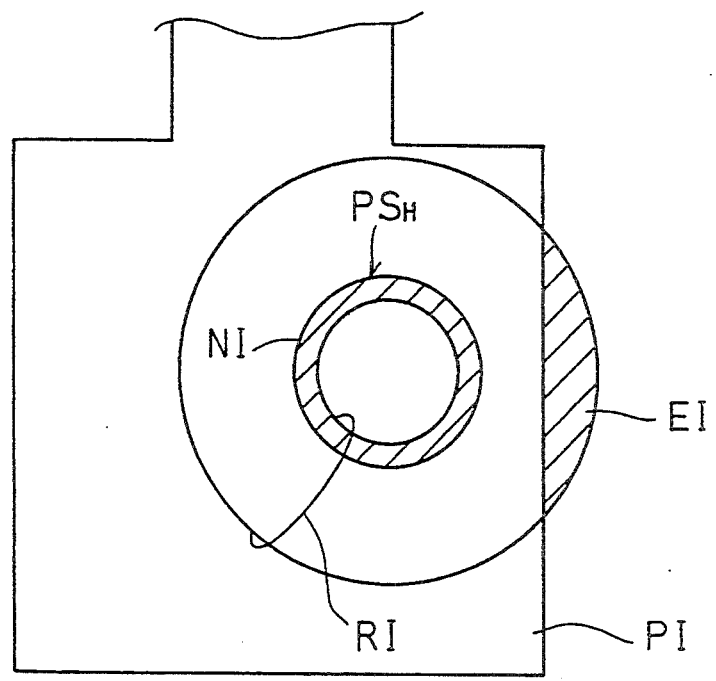
FIGS. 26 and 27 illustrate effects by double enlargement of a hole image, respectively.

The hole gauge image HGI and the pattern gauge image PGI are used for obtaining the protrusion region image EI. Since the peripheral portion of the hole gauge image HGI is relevant to the protrusion region image EI as mentioned above, the ring-like image RI shown in FIG. 1 can be used as the hole gauge image HGI. The principle for generating the ring-like image RI is as follows:

As described with reference to FIGS. 8 and 9, the size of the hole image HI is sometimes smaller than that of the blank portion $PS_H$ of the pattern image PS because of light reflection or light scattering at the inner wall of the through hole 15. When the hole image HI itself is employed in place of the enlarged hole image EH1 for generating the ring-like image RI of FIG. 1, the size of a blank portion inside the ring-like image RI is smaller than that of the blank portion $PS_H$ of the pattern image PS, so that the output signal ES (FIG. 1) of the AND circuit 202 represents not only the protrusion region image EI but also an internal ring image NI, as shown in FIG. 26. As a result, when the operator OP is applied to the image represented by the signal ES, the internal ring image NI is also subjected to the operation. Then, a false result of "insufficient annular width" might be obtained even if the minimum annular width is a sufficient one.

Figure 27:
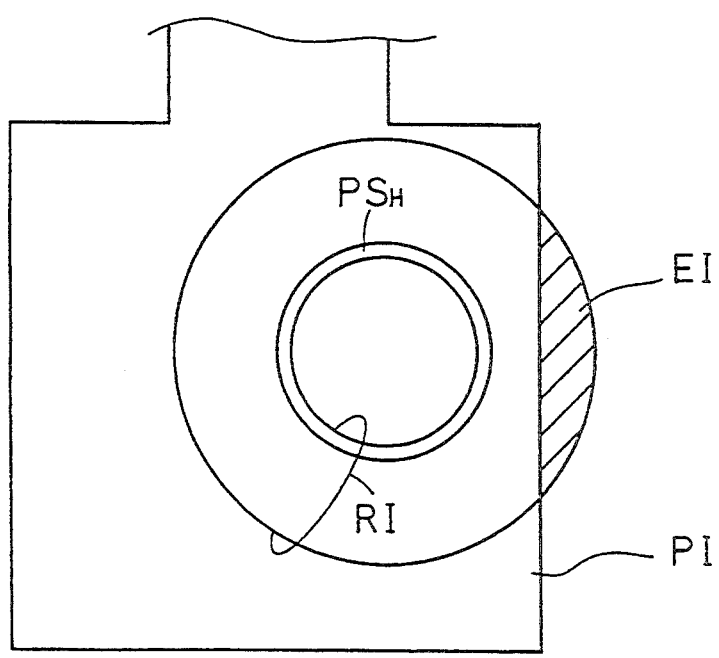
Figure 28:
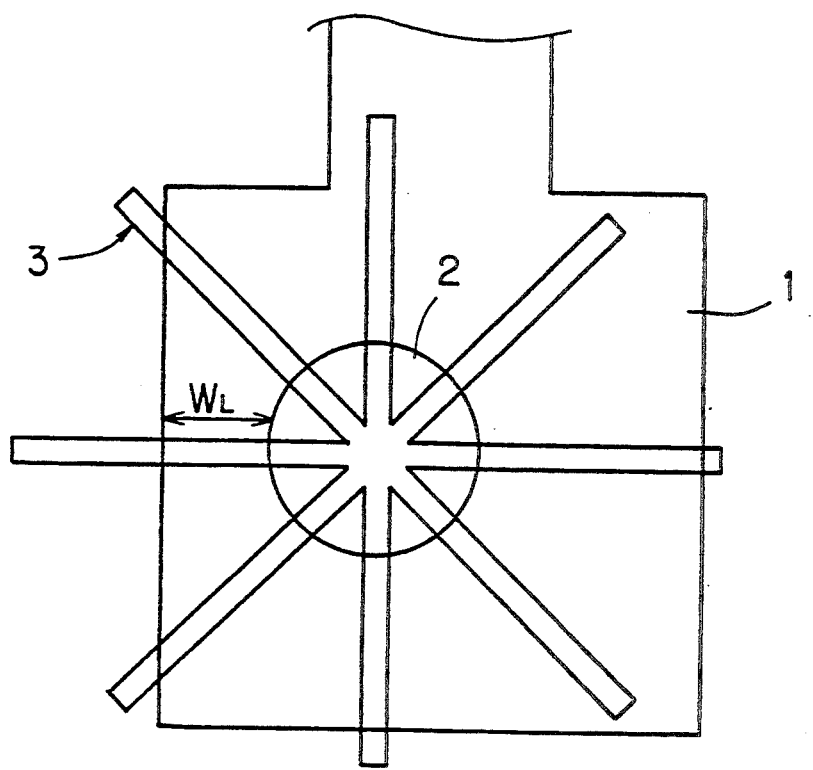
FIG. 28 illustrates a conventional inspection of a minimum annular width using a radial operator.

On the other hand, when the ring-like image RI based on the difference between the first and second enlarged hole images EH1 and EH2 determined in advance as shown in FIG. 1 is employed, the blank portion $PS_H$ of the pattern image PI is prevented from overlapping the ring-like image RI as shown in FIG. 27. This operation is advantageous in that the inspection for determining the defective/non-defective in the minimum annular width can be accurately performed. However, when an optical system is used in which the size of the hole image HI approximately coincides with the size of the blank portion $PS_H$ of the pattern image PS, the ring-like image RI may be produced based on the difference between the enlarged ring-like image EH2 and the hole image HI itself. Further, when the size of the internal ring image NI can be estimated beforehand and the size of the operator OP is increased in proportion to the size of the internal ring image NI, the ring-like image RI may be produced based on the difference between the enlarged ring-like image EH2 and the hole image HI itself since the inspection result is not affected by the internal ring image NI.

When the first enlarged hole image EH1 is employed to obtain the ring-like image RI, the annular width of the image plane decreases. However, this decrease does not affect the inspection of the annular width, and is avoided in the improvement according to another preferred embodiment described later.

Figure 2:
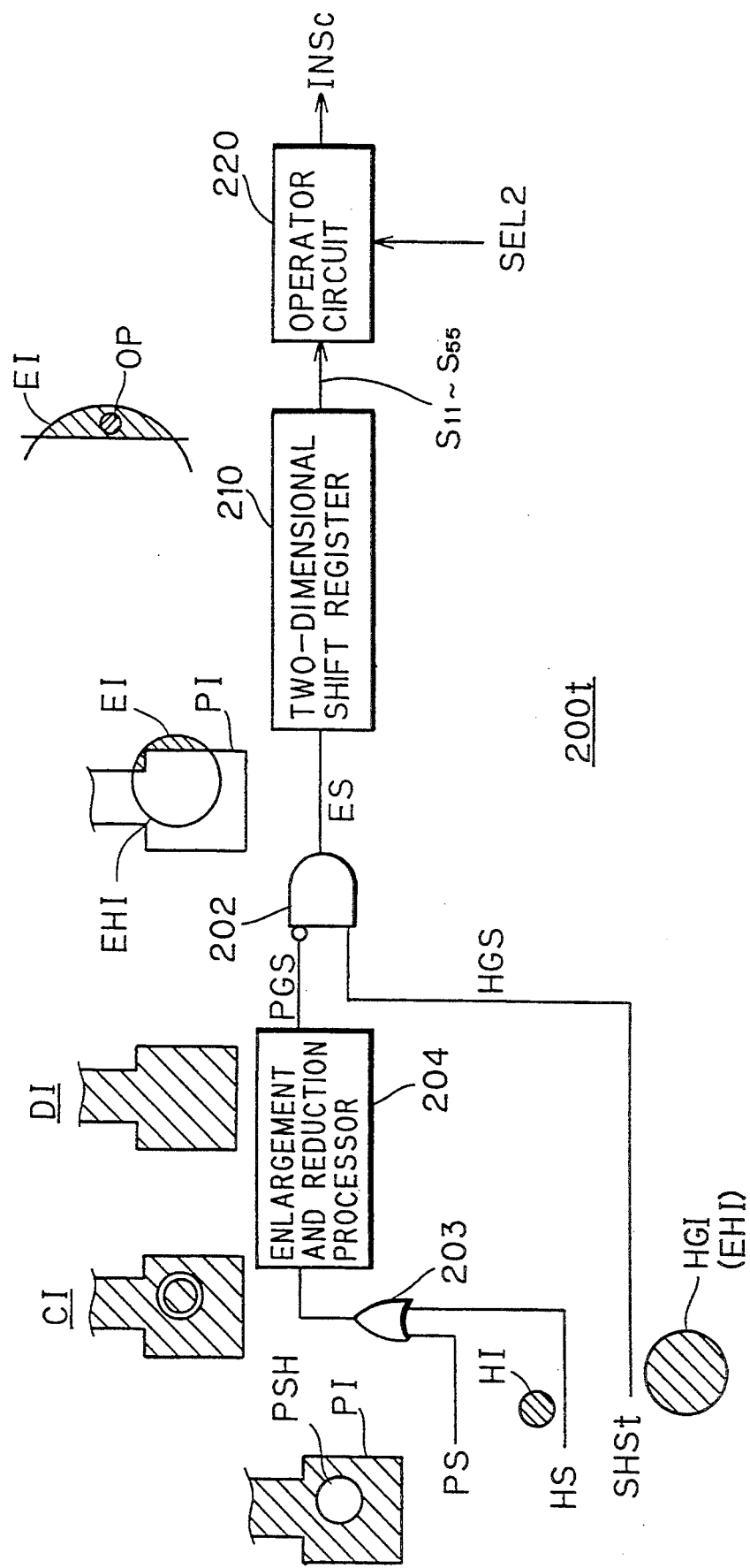
Figure 3:
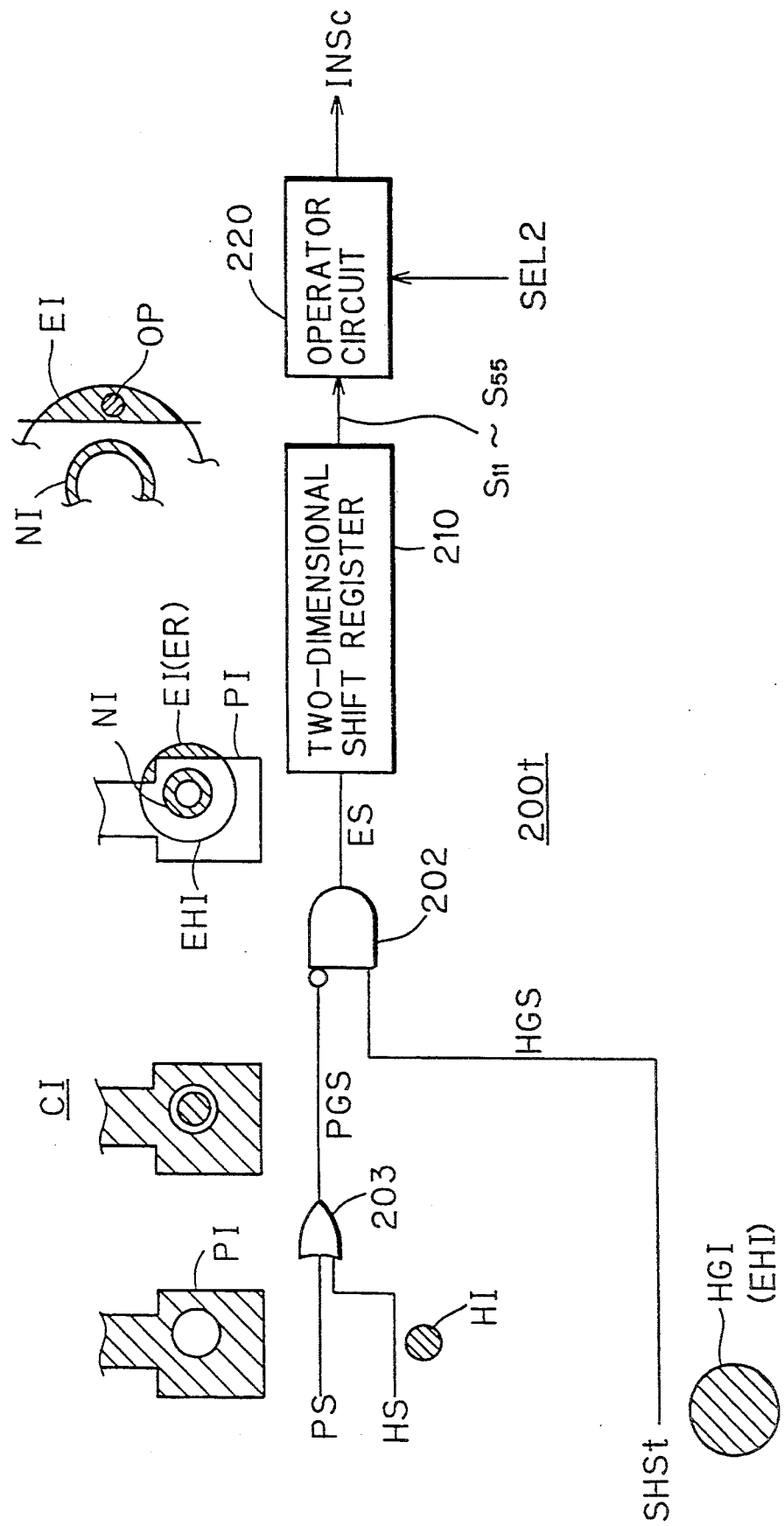

FIGS. 2 and 3 show preferred embodiments in which the enlarged hole image EHI is used as the hole gauge image HGI. Unlike the preferred embodiment shown in FIG. 1, the corrected pattern image CI (FIG. 3) in which the blank portion $PS_H$ is approximately compensated for or the corrected pattern image DI (FIG. 2) in which the blank portion $PS_H$ is completely compensated for is used as the pattern gauge image PGI.

G. Production of Pattern Gauge Image

The preferred embodiment of FIG. 2 is discussed first. To compensate for the blank portion $PS_H$ of the pattern image PI, the pattern image PI and the hole image HI are logically combined. That is, the signals PS and HS are input to an OR circuit 203. The corrected image CI thereby provided has a gap for the above-mentioned reason as shown in FIG. 2. The compensation for the gap is carried out by thickening the corrected image CI in an enlargement-and-reduction processor 204 to eliminate the gap and then shrinking the thickened image to the original size. The signal corresponding to the resultant corrected image DI is the pattern gauge image signal PGS. The inversion signal of the pattern gauge image signal PGS is applied to one terminal of the AND circuit 202.

The enlarged hole image EHI used as the hole gauge image HGI is sent as the signal $SHS_t$ from the enlargement circuit 120 (FIG. 10) similarly to the second enlarged hole image EH2 shown in FIG. 1. The signal $SHS_t$ is applied to the other terminal of the AND circuit 202 as the hole gauge image signal HGS. The AND circuit 202 outputs the protrusion region image signal ES.

Thus, when the corrected image DI including no blank portion $PS_H$ is used as the pattern gauge image PGI, the enlarged hole image EHI can be used as the hole gauge image HGI. The first enlarged hole image EH1 for defining the inner circumference of the ring-like image RI is not produced. Therefore, the above-mentioned substantial decrease of the minimum annular width is not caused, so that the minimum annular width can be inspected more accurately.

The pattern gauge image PGI may be the corrected pattern image CI before compensation for the gap in the preferred embodiment of FIG. 3. The internal ring image NI is produced in this case similarly to the case where the ring-like image RI is produced by using the hole image HI in place of the first enlarged hole image EHI. However, the minimum annular width can be inspected by selecting the operator OP of suitable size if the size of the internal ring image NI is estimated beforehand.

It is preferable that the size of the operator OP is variable for the above-mentioned reason. Another reason therefor is as follows:

H. Selection of Operator Size

Figure 19:
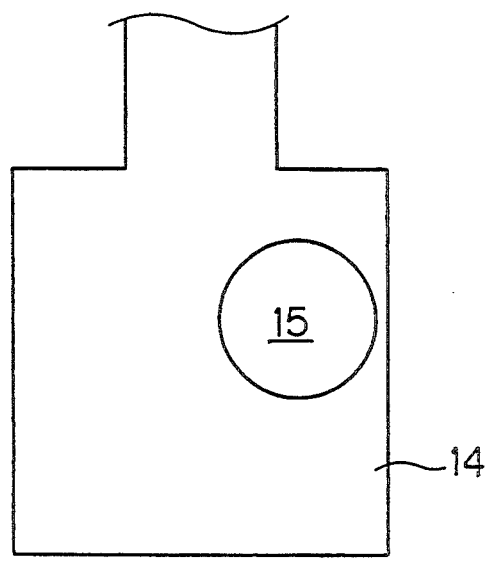
FIG. 19 illustrates the through hole in close proximity to an edge of the land.
Figure 20:
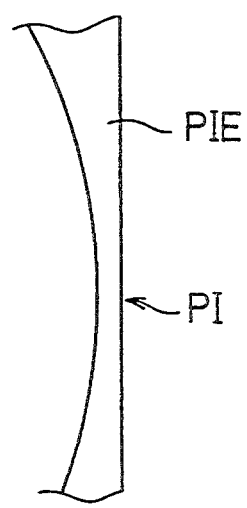
FIG. 20 illustrates an edge portion where the through hole is in close proximity to the edge of the land.
Figure 21:
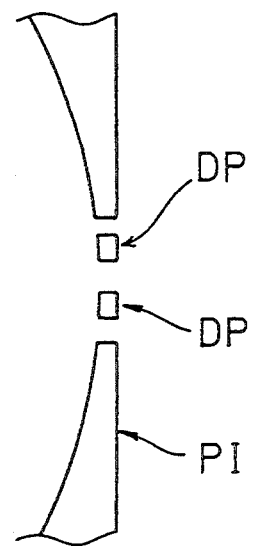
FIG. 21 illustrates a pattern image with hole breakout.

When the through hole 15 is in close proximity to the edge of the land 14 as shown in FIG. 19, an edge portion PIE of the pattern image PI is ideally expected to be an elongated and continuous image as shown in FIG. 20. In practice, resulting from errors in optical reading of the pattern image PI or in signal processing, the pattern image PI is sometimes broken as shown in FIG. 21 so that only dotlike images DP are left. In this case, the printed circuit board may be regarded as non-defective as far as an electric connection is attained at the through hole.

Figure 22:
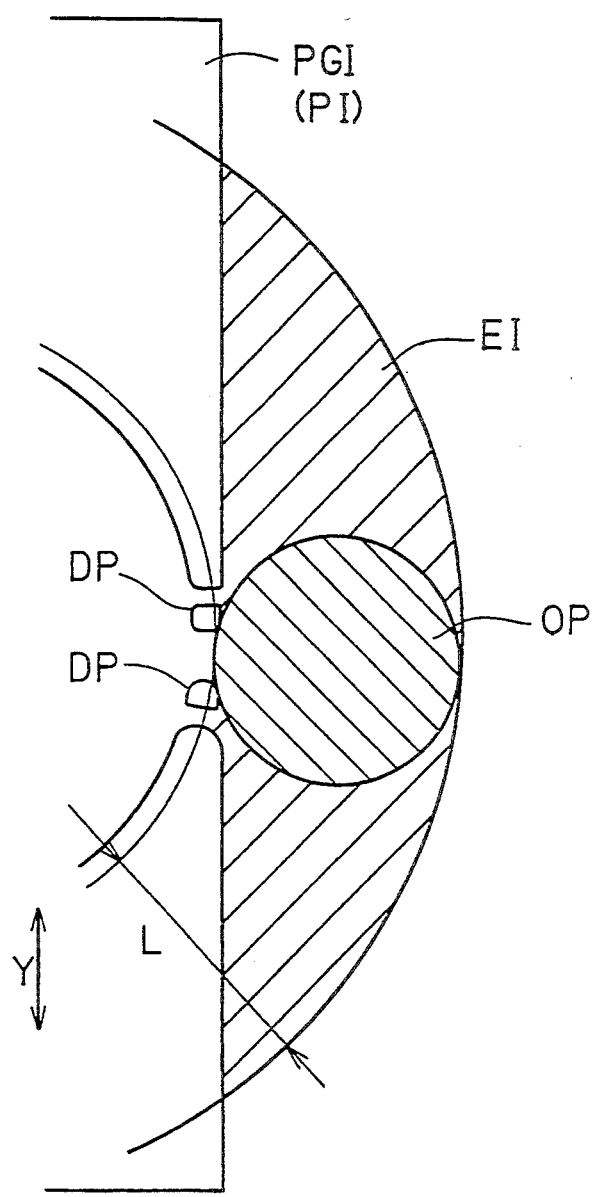
FIGS. 22 to 25 illustrate changes in operator size and in ring width, respectively.
Figure 24:
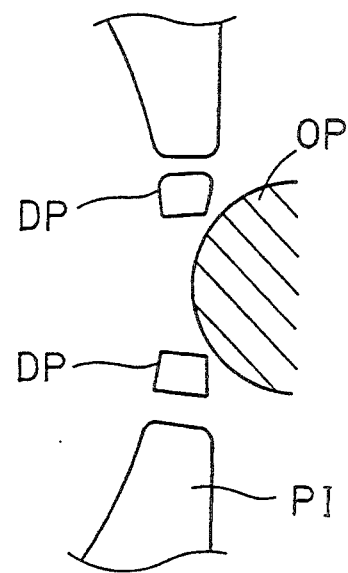

When the pattern gauge image PGI is determined from this pattern image PI, part of the operator OP enters the gap between the dotlike images DP in some cases as shown in FIGS. 22 and 24, so that the logical operation result by the operator OP becomes "1" (defective).

Figure 23:
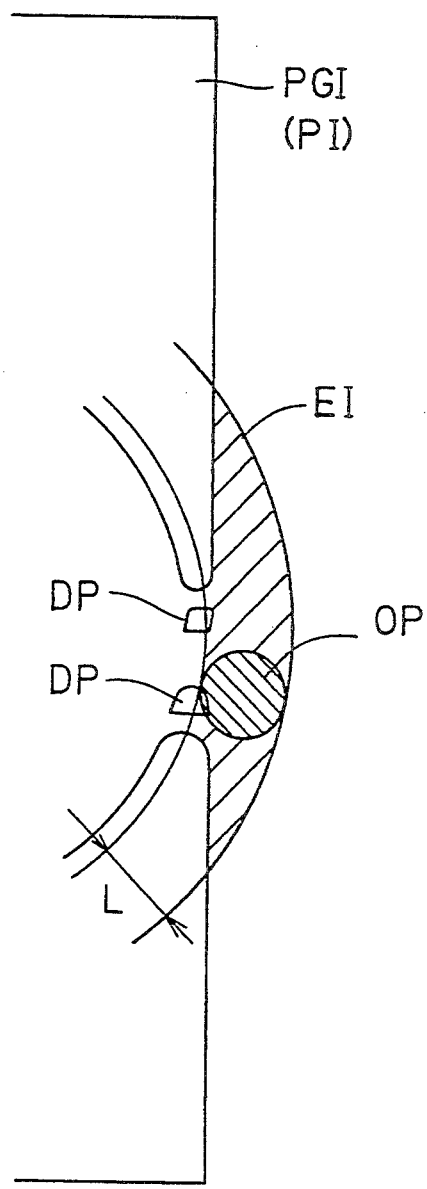
Figure 25:
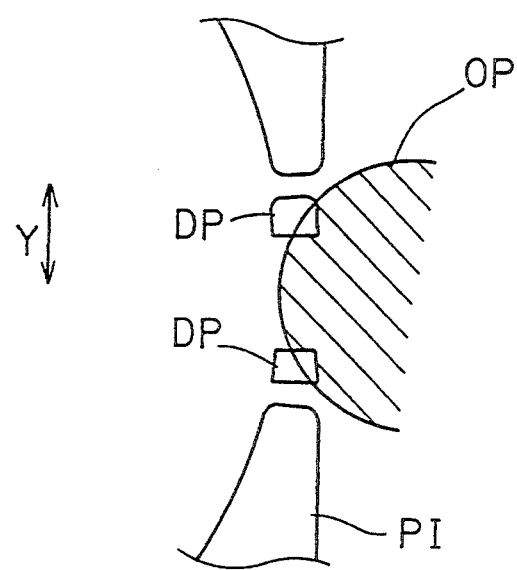

As shown in FIGS. 23 and 25, when the size of the operator OP is increased, the operator OP overlaps the dotlike images DP. The logical operation result by the operator OP constantly becomes "0" (non-defective) so that the aforesaid situation can be prevented. This structure is in general effective when the edge portion of the pattern gauge image PGI is broken without regard to the presence or absence of the dotlike images DP.

To increase the size of the operator OP, the output selection in the selector 226 of FIG. 14 is be changed. For example, when the broken edge of the pattern image PI which should be regarded as non-defective is decided to be defective by the operator $OP_9$, the selection signal SEL2 is changed through manual operation of the control panel 50 to change the output of the selector 226 from the logical product signal $PD_9$ to $PD_{12}$. If the logical product signal $PD_{12}$ is still insufficient, the output of the selector 226 is changed to $PD_{16}$ or $PD_{25}$. Conversely, when the size of the operator OP is so large that the pattern which should be regarded as defective is decided to be non-defective, the selection should be changed to the operator of smaller size. The same is true for the processing of the internal ring image NI described in the previous section G. When it is known in advance that the width of the internal ring image NI is smaller than the size of the operator $OP_9$, the size of the operator OP is selected among the sizes of the operators $OP_9$ to $OP_{25}$.

When only the size of the operator OP is changed in this operation, the reference value to determine whether the minimum annular width is sufficient or not is substantially deviated from a designated value. In this preferred embodiment, change in the size $L_r$ of the operator to be selected is accompanied by change in the width L of the hole gauge image HGI in accordance with the formula (6), so that the reference value $L_0$ is held at the same value as the value designated. That is when the size of the operator is changed from $L_r$ to $L_{r1}$, the width L is changed to $L_1$ obtained from the following formula:

$$L_1 = L + L_{r1} - L_r \qquad (7)$$

Thus the formula (8) corresponding to the formula (6) is always held.

$$L_1 - L_{r1} = L_0 \qquad (8)$$

When the size $L_r$ of the operator OP is increased, the width L is accordingly increased. When the size $L_r$ of the operator OP is decreased, the width L is, accordingly decreased. The calculation therefor is performed in the selection signal generator 51. The width L is changed by changing the selection signal SEL1 applied to the selector 133 (FIG. 11).

I. Modifications (1) The optical system for reading the printed circuit board may be a system in which respective images of the wiring pattern and the through hole are obtained only from reflected light. In this case, the obtained analog signal is binarized with two different threshold values to determine the pattern image PI and the hole image HI.

(2) It is preferable that the operator OP has a symmetrical shape such as a circle or a polygon to inspect the size of the protrusion region image EI with uniform accuracy, since the protrusion region image EI may protrude from the pattern image PI in any direction. The operator OP, however, may be of other shape whose maximum width is of the designated size.

(3) The present invention is also applicable to a case where the land is a circular or other-shaped land.

While the invention has been shown and described in detail, the foregoing description is in all aspects illustrative and not restrictive. It is therefore understood that numerous modifications and variations can be devised without departing from the scope of the invention.

We claim:

1. A method of inspecting a minimum annular width of a land formed on a printed circuit board which is provided thereon with a wiring pattern having said land and a through hole perfectly or imperfectly surrounded by said land, said method comprising the steps of:
   (a) obtaining a pattern image representing the shape of said wiring pattern and a hole image representing the shape of said through hole;
   (b) converting said hole image into a hole gauge image having a diameter larger than a diameter of said hole image;
   (c) obtaining a pattern gauge image having a contour of the same shape as said pattern image;
   (d) obtaining a protrusion region image having a width which is representative of part of said hole gauge image which protrudes from said pattern gauge image; and
   (e) scanning said protrusion region image with a circle operator having a solid, substantially circular shape and a size corresponding to a reference value and applying said circle operator to said protrusion region image simultaneously with said scanning to thereby determine whether said circle operator can be located completely within said protrusion region image to determine whether the minimum annular width of said land is larger than said reference value.

2. The method of claim 1, wherein said operator consists of a cluster of pixels.

3. The method of claim 2, wherein said cluster of pixels is a matrix array of pixels.

4. The method of claim 2, wherein said cluster of pixels is a cross-shaped array of pixels.

5. The method of claim 1, wherein the step (c) comprises the step of:
   (c-1) defining said pattern gauge image by said pattern image itself.

6. The method of claim 5, wherein the step (b) comprises the steps of:
   (b-1) enlarging said hole image by first and second enlargement widths which are different from each other, to obtain first and second enlarged hole images, respectively; and
   (b-2) logically combining said first and second enlarged hole images to form a ring-like image around said hole image, said ring-like image being defined as said hole gauge image.

7. The method of claim 6, wherein: the step (e) comprises the steps of:
   (e-1) designating said reference value; and
   (e-2) determining a ring width of the ring-like image and the diameter of said operator as a function of said reference value.

8. The method of claim 7, wherein the step (e-2) comprises the steps of:
   (e-2-1) preparing a plurality of operators having different sizes;
   (e-2-2) selecting one of said plurality of operators according to said reference value to specify said operator; and
   (e-2-3) determining said ring width of said ring-like image as a function of the diameter of said operator selected and said reference value.

9. The method of claim 1, wherein the step (b) comprises the step of:
   (b-3) enlarging said hole image to define the hole gauge image.

10. The method of claim 9, wherein the step (c) comprises the steps of:
    (c-2) logically combining said pattern image and said hole image to obtain a corrected image; and
    (c-3) obtaining said pattern gauge image from said corrected image.

11. The method of claim 10, wherein
    said pattern image has an annular image corresponding to said land; and a circular blank area which is surrounded by said annular image, said circular blank area having a diameter larger than said hole image; and the step (c-3) comprises the step of:
    (c-3-1) thickening respective parts of said corrected image to obtain an enlarged and corrected image in which said circular blank area is eliminated; and
    (c-3-2) shrinking respective parts of said enlarged and corrected image to obtain said pattern gauge image.

12. An apparatus for inspecting a minimum annular width of a land formed on a printed circuit board which is provided thereon with a wiring pattern having said land and a through hole perfectly or imperfectly surrounded by said land, said apparatus comprising:
    (a) means for obtaining a pattern image representing the shape of said wiring pattern and a hole image representing the shape of said through hole;
    (b) means for converting said hole image into a hole gauge image having a diameter larger than a diameter of said hole image;
    (c) means for obtaining a pattern gauge image having a contour of the same shape as said pattern image;
    (d) means for obtaining a protrusion region image having a width which is representative of part of said hole gauge image which protrudes from said pattern gauge image; and (e) means for comparing the width of said protrusion region image with a predetermined reference value to determine whether the minimum annular width of said land is larger than said reference value or not, said means for comparing comprising:

(e-1) means for scanning said protrusion region image with a circle operator having a solid, substantially circular shape and a size corresponding to said reference value; and (e-2) means for applying said circle operator to said protrusion region image simultaneously with said scanning to thereby determine whether said circle operator can be located completely within said protrusion region image to determine if the minimum annular width of said land is larger than said reference value.

13. The apparatus of claim 12, wherein said operator consists of a cluster of pixels.

14. The apparatus of claim 13, wherein said cluster of pixels is a matrix array of pixels.

15. The apparatus of claim 13, wherein said cluster of pixels is cross-shaped array of pixels.

16. The apparatus of claim 12, wherein the means (c) comprises:

(c-1) means for defining said pattern gauge image by said pattern image itself.

17. The apparatus of claim 16, wherein the means (b) comprises:

(b-1) means for enlarging said hole image by first and second enlargement widths which are different from each other to obtain first and second enlarged hole images, respectively; and (b-2) means for logically combining said first and second enlarged hole images to form a ring-like image around said hole image, said ring-like image being defined as said hole gauge image.

18. The apparatus of claim 17, wherein the means (e) comprises:

(e-3) means for inputting a signal designating said reference value; and (e-4) means for determining a ring width of the ring-like image and the diameter of said operator as a function of said reference value.

19. The apparatus of claim 18, wherein the means (e-4) comprises:

(e-4-1) means for holding a plurality of operators having different sizes;

(e-4-2) means for selecting one of said plurality of operators according to said reference value to specify said operator; and (e-4-3) means for determining said ring width of said ring-like image as a function of the diameter of said operator selected and said reference value.

20. The apparatus of claim 12, wherein the means (b) comprises:

(b-3) means for enlarging said hole image to define the hole gauge image.

21. The apparatus of claim 20, wherein the means (c) comprises:

(c-2) means for logically combining said pattern image and said hole image to obtain a corrected image; and (c-3) means for obtaining said pattern gauge image from said corrected image.

22. The apparatus of claim 21, wherein said pattern image has an annular image corresponding to said land; and a circular blank area which is surrounded by said annular image, said circular blank area having a diameter larger than said hole image; and the means (c-3) comprises:

(c-3-1) means for thickening respective parts of said corrected image to obtain an enlarged and corrected image in which said circular blank area is eliminated; and (c-3-2) means for shrinking respective parts of said enlarged and corrected image to obtain said pattern gauge image.

* * * * *